(12) United States Patent
Nuijs et al.

(10) Patent No.: US 8,414,566 B2
(45) Date of Patent: Apr. 9, 2013

(54) PHOTO-EPILATION DEVICE

(75) Inventors: Antonius Maarten Nuijs, Eindhoven (NL); Lenie Johanna Theodora Evers-Derkx, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/919,035

(22) PCT Filed: Mar. 2, 2009

(86) PCT No.: PCT/IB2009/050817
§ 371 (c)(1),
(2), (4) Date: Aug. 24, 2010

(87) PCT Pub. No.: WO2009/109885
PCT Pub. Date: Sep. 11, 2009

(65) Prior Publication Data
US 2011/0004201 A1    Jan. 6, 2011

(30) Foreign Application Priority Data
Mar. 7, 2008   (EP) .................................... 08152423

(51) Int. Cl.
*A61B 18/18* (2006.01)

(52) U.S. Cl. .......................................................... 606/9

(58) Field of Classification Search .................. 606/9–12
See application file for complete search history.

(56) References Cited

U.S. PATENT DOCUMENTS

| 5,735,844 | A | 4/1998 | Anderson et al. |
| 6,080,147 | A | 6/2000 | Tobinick |
| 6,280,438 | B1 | 8/2001 | Eckhouse et al. |
| 7,044,959 | B2 | 5/2006 | Anderson et al. |
| 7,175,617 | B2 | 2/2007 | Jay |
| 2004/0167501 | A1 | 8/2004 | Island et al. |
| 2004/0230260 | A1 | 11/2004 | MacFarland et al. |
| 2006/0116669 | A1* | 6/2006 | Dolleris ......................... 606/17 |
| 2006/0247740 | A1* | 11/2006 | Roersma et al. ................ 607/86 |
| 2006/0293728 | A1 | 12/2006 | Roersma et al. |

FOREIGN PATENT DOCUMENTS

| EP | 0788814 A2 | 8/1997 |
| WO | 9623447 A1 | 8/1996 |
| WO | 9934867 A1 | 7/1999 |
| WO | 03103523 A1 | 2/2003 |
| WO | 2005074830 A2 | 8/2005 |
| WO | 2007099546 A1 | 9/2007 |

OTHER PUBLICATIONS

"Target Chromophore Efficiency-Super-Selective Photothermolysis ('SSP')"; Sybaritic, Inc. Advertisement for Their Nanno Light Product, 6 Page Document.
Drosner et al: "Low Dose Epilation by Alexandrite Laser: A Dosee Response Study"; Med. Laser Appl., vol. 16, 2001, pp. 293-298.

* cited by examiner

Primary Examiner — James Greece

(57) ABSTRACT

A photo-epilation device including a hand-held housing with at least one window opening; a lamp accommodated in the housing for generating light having a spectral range from approximately 575 nm to approximately 1700 nm; and a control device for driving the lamp. The lamp is switched on in brief pulses having a pulse duration in the range from 1.1 ms to 1.9 ms, and a pulse repetition frequency in the range from 0.1 Hz to 0.5 Hz. The fluence on skin level is in the range from 2 to 7 J/cm2, dependent on the skin type.

14 Claims, 1 Drawing Sheet

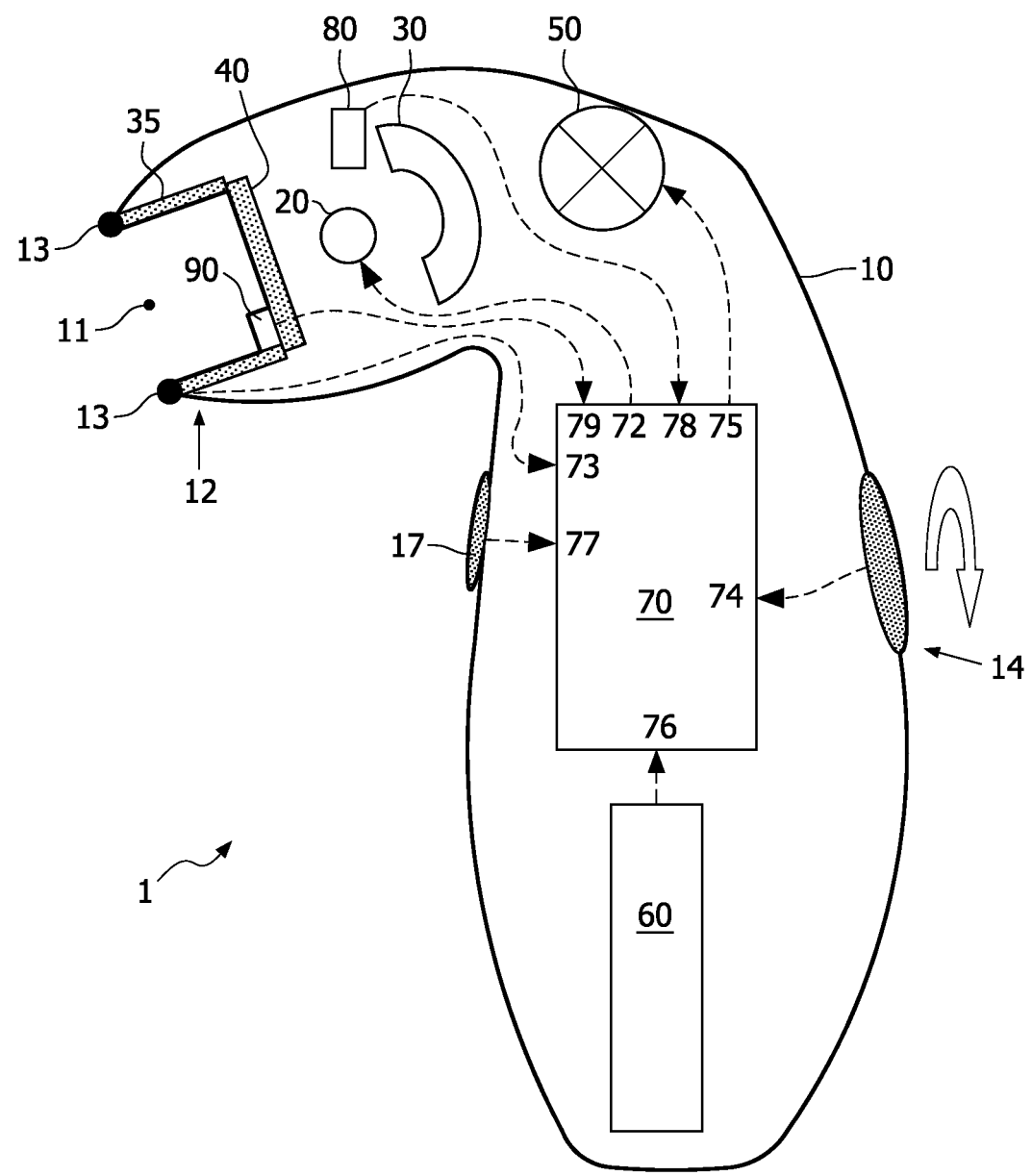

PHOTO-EPILATION DEVICE

FIELD OF THE INVENTION

The present invention relates in general to photo-epilation, i.e. (temporary or permanent) hair removal by light.

BACKGROUND OF THE INVENTION

Photo-epilation is known per se; by way of example, reference is made to U.S. Pat. No. 5,735,844. Light originating from a suitable light source (laser; flash lamp) is absorbed by melanin in a hair and/or follicle. The absorbed light is converted into heat. This heat damages or even destroys the follicle. The hair is shed, and new growth is delayed or even fully prevented.

The light is typically applied in pulses. There are several parameters that play a role in epilation efficiency: pulse duration, pulse repetition frequency, wavelength or spectral range of the light, and fluence (or energy density, expressed in $J/cm^2$). When permanent hair removal and thus follicle destruction is intended, literature reports fluences as high as 60 $J/cm^2$ applied in pulses in the range from a few ms to a few hundred ms. U.S. Pat. No. 7,044,959 discloses a method for temporary reduction of hair growth using a broad range of parameter settings for both pulsed sources and continuous sources in scanning motion. In an article "Low dose epilation by alexandrite laser: a dose response study" in Med.Laser Appl., vol. 16, 2001, pp. 293-298, M. Drosner et al. describe a study of hair removal using a relatively low-power alexandrite laser. The wavelength is 890 nm, the fluence is from 5 to 10 $J/cm^2$, the pulse duration is 7 ms. The authors observed long-time hair removal, but they express doubts on the permanency of their method.

SUMMARY OF THE INVENTION

Professional systems in practice typically aim to apply high fluences in order to obtain permanent hair removal. However, a problem is that there are different skin types. If the fluence is too low for a certain skin type, the obtained result may be unsatisfactory. If the fluence is too high for a certain skin type, the melanin in the epidermis will absorb too much light and, consequently, undesirable effects such as blistering and/or hyperpigmentation, and/or high levels of pain are likely to occur. Therefore, when working with such professional systems, the parameters must be set by well-trained professionals in order to ensure that the parameter settings are in conformity with the relevant patient's skin type. Furthermore, treatments with high fluence must be combined with skin cooling in order to alleviate pain and prevent skin damage. Such professional systems are bulky, heavy, and expensive. Consequently, they are not suitable for the consumer market.

In another approach, aiming to reduce the overall size of the apparatus, high fluence is achieved by reducing the "footprint", i.e. the skin area that can be treated. In a commercially available photo-epilation device, intended for the consumer market, the fluence is as high as 18 $J/cm^2$ at a treatment window as low as 0.8 $cm^2$. This obviously makes treatment of a substantial skin area such as an entire leg uncomfortably slow and tedious.

It is an object of the present invention to provide a photo-epilation device that can be comfortably used by consumers at home, with little or no risk of side effects, and with little or no risk of unacceptably high levels of pain.

It is a further object of the present invention to provide a photo-epilation device that can be used by consumers of all skin types, without the need of well-trained professionals for operating the device.

It is another object of the present invention to provide a photo-epilation device that is relatively small. Particularly, the present invention has for its object to provide a hand-held and easily transportable photo-epilation device.

In accordance with an important aspect of the present invention, a low fluence setting which is still effective is chosen, dependent on the skin type. This keeps heat generation low, and thus allows effective cooling to be achieved by a simple fan blowing ambient air at a low flow rate, and ultimately allows a smaller size of the apparatus.

A device according to the present invention has the features as defined in claim 1. Further advantageous and preferred features are defined in the dependent claims.

It is noted that some prior-art systems comprise a base station and a handpiece. A device according to the present invention is distinguished by the absence of a base station and a coupling between the base station and the handpiece, because both the lamp and the controller are accommodated in the hand-held housing. The device according to the present invention is thus fully self-contained.

BRIEF DESCRIPTION OF THE DRAWING

These and other aspects, features and advantages of the present invention will be further explained in the following description of one or more preferred embodiments with reference to the drawing, in which identical reference numerals indicate the same or similar parts, and in which:

FIG. 1 schematically illustrates a hand-held photo-epilation device according to the present invention.

DESCRIPTION OF EMBODIMENTS

FIG. 1 schematically illustrates a hand-held photo-epilation device 1 according to the present invention. The device comprises a housing 10, the size of which is comparable to the size of a shaving device. The housing 10 accommodates at least one intense broadband light source 20. The light source 20, hereinafter also referred to as "lamp", is suitably implemented as a Xenon flash lamp, but other types of lamps may also be used, provided they produce a light spectrum which is suitable to achieve photo-epilation. Since Xenon flash lamps are known per se, a further explanation is not necessary.

The housing 10 is substantially closed, yet has one window opening 11 (although the housing may also have a plurality of window openings) for allowing light generated by the lamp 20 to exit the housing. The edges of the window opening 11 will be referred to as the mouth 12 of the device 1. A preferred shape of the window opening is substantially rectangular, and a preferred size is approximately 30 mm×approximately 10 mm. For treating small skin portions, it may, however, be desirable that the window opening has a smaller size, for instance, about 15 mm×10 mm. The window opening may be provided with moveable shutters to reduce the exit opening. Adjacent the lamp 20, opposite the window opening 11, a reflector 30 is arranged so as to increase the portion of the generated light that exits the housing and to increase the efficiency of the light output and reduce the amount of light wasted within the housing. The reflector 30 may be suitably curved, as illustrated, so as to concentrate the light output. It is noted that the reflector 30 may be replaced by a system of multiple reflectors.

Xenon flash lamps are capable of generating intense light within a spectral range from ultraviolet to infrared, i.e. from less than 575 nm to as high as 1700 nm. Ultraviolet light may be harmful. Hence, it is preferred that this light is filtered out. To this end, a filter 40 arranged between the lamp 20 and the window opening 11 is selected to stop UV light and preferably selected to stop light having a wavelength below approximately 575 nm; the edge of this range is not critical. Since suitable filters are known per se, a further explanation is not needed here. It is noted that a designer may select a different filter having a different characteristic so that the spectral range which is blocked differs slightly.

The spectrum above approximately 1000-1200 nm hardly contributes or does not contribute to photo-epilation. Therefore, it is also possible to add a filter for stopping light having a wavelength above approximately 1200 nm, which edge is neither critical. However, within the context of the present invention, such filtering is not needed.

Adjacent the window opening 11, within the housing, a system of mirrors 35 defines a light path for the light travelling from the filter 40 to the window opening 11 and thus to the skin to be treated. These mirrors, which may be made of, for instance, polished metal, reflect light which is not exactly travelling towards the window opening 11, again in order to increase the efficiency of the light output and reduce the amount of light wasted within the housing.

A fan 50 for cooling the lamp 20 is arranged inside the housing. It generates an air flow that is passed along the lamp so as to cool it. The housing may have exit openings (not shown) for allowing the air flow to exit the housing; these exit openings may be arranged close to the window opening 11. The housing may also have entry openings (not shown) for allowing air to enter the housing.

The housing 10 also accommodates a battery 60 for powering the lamp 20 and the fan 50, controlled by an electronic control device 70 typically comprising a micro-controller or microprocessor or the like. The control device 70 has a supply input 76 which is coupled to the battery for receiving the battery power. It is noted that the battery 60 may be replaceable when empty, but it may also be a rechargeable battery, and that the housing 10 is provided with a connector (not shown) for connection to a charging device, typically implemented as a mains adapter. Alternatively, the battery may also be recharged by a circuit receiving electromagnetic energy in a wireless manner and comprising, to this end, a reception coil (not shown) arranged in the housing 10. Since such a technology for charging a battery is known per se, a further explanation is not needed here.

The control device 70 further has a lamp output 72 which is coupled to the lamp 20 for controlling the lamp operation. The control device 70 also has a fan output 75 which is coupled to the fan 50 for controlling the fan operation.

The housing 10 is provided with a user-operated control member 17 for switching the photo-epilation device 1 on or off. This control member 17 may be implemented as a push-button switch, a slider switch, etc., as are known per se. In the embodiment shown, the control device 70 further has a user control input 77 which is coupled to the control member 17 and allows the control device 70 to decide on the lamp operation and fan operation on the basis of the position of the control member 17. Alternatively, the control member 17 may also be associated with the battery 60 for switching the battery power on or off.

Suitable operation parameters depend on the user's skin type. Therefore, the control device 70 is responsive to a user-operated input member 14, connected to a user input 74, for setting one or more operation parameters. It is generally recognized that there are six different skin types. Therefore, a suitable input member 14 is, for instance, a rotary knob with six positions for selecting a certain skin type.

It is noted that, alternatively or in addition to selecting one of the six skin types, the input member 14 may allow some fine adjustment.

Furthermore, it is noted that the input member 14 and the user-operated control member 17 may be integrated. For instance, the input member 14 may have a seventh position being the OFF position.

Instead of a manual selector to be set by the user, the device 1 may also comprise a skin-type detector 90 which is mounted close to the window opening 11 for receiving reflected light reflected backwards from the skin and is capable of generating a skin-type detector signal based on the color or spectral distribution of the reflected light. In such a case, the control device 70 has a skin-detector input 79 which is coupled to the skin-type detector 90.

The device may also comprise such a skin-type detector 90 in combination with a user-operated input member 14. In such a case, the skin-type detector signal may result in, for instance, a general selection by the control device 70 from among the six skin types, while the user-operated input member 14 may effect a fine setting within the general skin-type setting range.

In principle, it is possible to switch on the lamp 20 immediately when the user activates the ON button 17. However, this is not preferred, because it is desirable that the high-intensity light is only generated when needed, i.e. when the mouth 12 is applied to a user's skin. The device 1 therefore preferably comprises at least one skin-contact sensor 13 which generates a contact signal upon contact with the user's skin. The control device 70 further has a skin-contact input 73 which is coupled to the skin-contact sensor 13, and only actuates the lamp 20 if the signal received at its skin-contact input 73 indicates skin contact. The skin-contact sensor 13 may be, for instance, a mechanical sensor that is displaced upon skin contact, an optical sensor, an ultrasonic sensor, a capacitive sensor, etc.

More preferably, the device 1 comprises a plurality of skin-contact sensors arranged on opposite sides of the mouth 12, and the control device 70 only actuates the lamp 20 if the signals received from all skin-contact sensors indicate skin contact.

In operation, the control device 70 controls the lamp 20 such that it is switched on in brief pulses having a pulse duration in the range from 1 ms to 2 ms. The lower limit of this range is preferably higher than 1 ms, preferably 1.1 ms. The higher limit of this range is preferably lower than 2 ms, preferably 1.9 ms. A preferred setting of the pulse duration is about 1.8 ms. In this context, the pulse duration is measured at 50% of the maximum light intensity, because it takes some time for the lamp to build up the light intensity from zero while it also takes some time for the lamp to reduce its light intensity back to zero.

The fluence on skin level is in the range from 2 to 7 $J/cm^2$ (integrated over an effective spectral range from 575 nm to 1000 nm) per pulse, dependent on the skin type. It is noted that any radiation in the spectral range above 1000 nm is not taken into account in the above fluence value.

A commonly used skin-classification system was devised in 1975 by Thomas B. Fitzpatrick, MD, PhD, of Harvard Medical School. This skin-classification system is based on a person's complexion and responses to sun exposure and comprises the following types with the following characteristics:

| | | |
|---|---|---|
| TYPE I: | Pale white skin, blond/red hair | Always burns, does not tan |
| TYPE II | fair skin | burns easily |
| TYPE III | dark white skin | burns, then tans |
| TYPE IV | light brown skin | tans easily with minimum burns |
| TYPE V | medium brown skin | tans darkly with rarely burns |
| TYPE VI | dark brown skin | tans darkly, never burns |

As mentioned hereinbefore, the input member 14 may allow the user to input a skin type, and the user may obtain, for instance, the information relating to his or her skin type from a descriptive manual, or from example images, or the like. For skin types according to this Fitzpatrick system, the control device 70 sets the fluence on skin level in the range from:
5 to 7 $J/cm^2$ for skin types I, II, III;
4 to 6 $J/cm^2$ for skin type IV;
3 to 5 $J/cm^2$ for skin type V; and
2 to 3 $J/cm^2$ for skin type VI.

Typically, if the input member 14 is only capable of inputting a skin type, the control device 70 preferably sets the fluence on skin level at the maximum value of said ranges, i.e. at
about 7 $J/cm^2$ for skin types I, II, III;
about 6 $J/cm^2$ for skin type IV;
about 5 $J/cm^2$ for skin type V; and
about 3 $J/cm^2$ for skin type VI.

Typically, if the input member 14 allows the user to set, in accordance with his or her specific tolerance or sensitivity, a fine tuning in a range from MINIMUM to MAXIMUM, the control device 70 preferably sets the fluence on skin level at the maximum value of said ranges when the user selects MAXIMUM, i.e. at
about 7 $J/cm^2$ for skin types I, II, III;
about 6 $J/cm^2$ for skin type IV;
about 5 $J/cm^2$ for skin type V; and
about 3 $J/cm^2$ for skin type VI;
and preferably sets the fluence on skin level at the minimum value of said ranges when the user selects MINIMUM, i.e. at
about 5 $J/cm^2$ for skin types I, II, III;
about 4 $J/cm^2$ for skin type IV;
about 3 $J/cm^2$ for skin type V; and
about 2 $J/cm^2$ for skin type VI.

The user may not be required to input his or her settings in terms of skin type, as the input member allows the user to select a continuous fluence setting from MINIMUM to MAXIMUM. The input member may be implemented, for instance, as a rotary knob, and the control device 70 sets the fluence on skin level at a value in the range from 2 to 6/$cm^2$ in linear dependence upon the user setting (the rotary position of the knob) between MINIMUM and MAXIMUM.

For epilation purposes, the fluence as mentioned above should be offered to the skin within a time frame having a duration as mentioned above. In this respect, it is not important whether the light within the time frame is offered continuously, i.e. as one continuous light flash or continuous pulse, or whether the light within the time frame is offered intermittently, i.e. as a train of sub-pulses, in which case the train will still be indicated as "pulse". Multiple light pulses for the same skin area are not needed. For treating a skin area larger than the footprint (i.e. the size of the window 11) of the device, the user has to displace the device from one skin area to another and repeat the treatment. The device may have a user-controllable trigger input, for instance, a push-button, which the user operates when he is ready to apply the next single light pulse. The control device 70 may also drive the lamp repetitively, for instance, at a pulse repetition frequency in the range from 0.1 Hz to 0.5 Hz, allowing the user time to displace the device between pulses. As mentioned hereinbefore, a light pulse is preferably not applied if there is no skin contact.

In professional systems, with high fluence, it is necessary to filter out light having a wavelength of more than 1000 nm in order to alleviate pain. At the relatively low fluence, the present invention precludes the necessity to remove these wavelengths, thus providing a saving. Furthermore, in view of the relatively low fluence, the lamp generates relatively little heat, which can be removed by means of a simple fan and thus avoids the need of using complicated and heavy water-cooling devices. Moreover, also in view of the relatively low fluence, it is not necessary to cool the skin by means of a gel or the like.

The device 1 is preferably provided with temperature-sensing means for generating a signal indicating the lamp temperature, for instance, a temperature sensor 80 mounted close to the lamp 20 to sense its temperature. The control device 70 further has a temperature input 78 which is coupled to the temperature sensor 80. The control device 70 compares the temperature signal with a predetermined threshold signal and ensures that the lamp 20 is only operated as long as the lamp temperature is below the threshold temperature.

While the invention has been illustrated and described in detail in the drawing and the foregoing description, it should be clear to a person skilled in the art that such an illustration and description are to be considered illustrative or as examples and that they are not restrictive. The invention is not limited to the disclosed embodiments; rather, several variations and modifications are possible within the protective scope of the invention as defined in the appended claims.

For instance, instead of or in addition to being battery-powered, the device may be provided with a power cord for connection to the mains.

Furthermore, the operating range of 545 nm to 1200 nm is a preferred range, but slight variations of the limits of this range are possible. It is sufficient if the light is generated in a broad spectral range suitable for effecting photo-epilation.

Furthermore, the window may be sub-divided.

Features described in relation to a particular embodiment can also be applied to other embodiments described. Features of different embodiments may be combined to achieve another embodiment. Features not explicitly indicated as being essential may be omitted.

Other variations to the disclosed embodiments can be understood and effected by those skilled in the art in practicing the claimed invention, from a study of the drawing, the disclosure, and the appended claims. In the claims, use of the verb "comprise" and its conjugations does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims shall not be construed as limiting the scope.

The present invention has been explained with reference to a block diagram which illustrates functional blocks of the device according to the present invention. It is to be understood that one or more of these functional blocks may be implemented in hardware, wherein the function of such a functional block is performed by individual hardware components, but one or more of these functional blocks may also be implemented in software, so that the function of such a functional block is performed by one or more program lines of a computer program or a programmable device such as a microprocessor, microcontroller, digital signal processor, etc.

In summary, the present invention provides a photo-epilation device 1, which comprises:

a hand-held housing 10 with at least one window opening 11;
a lamp 20 accommodated in the housing for generating light having a spectral range from
approximately 575 nm to approximately 1200 nm; and
control device 70 for driving the lamp 20.

The lamp is switched on in brief pulses having a pulse duration in the range from 1 ms to 2 ms, preferably from 1.1 ms to 1.9 ms, more preferably about 1.8 ms, and a pulse repetition frequency in the range from 0.1 Hz to 0.5 Hz.

The fluence on skin level is in the range from 2 to 7 J/cm$^2$, dependent on the skin type, particularly from:
5 to 7 J/cm$^2$ for skin types I, II, III;
4 to 6 J/cm$^2$ for skin type IV;
3 to 5 J/cm$^2$ for skin type V; and
2 to 3 J/cm$^2$ for skin type VI.

The invention claimed is:

1. A photo-epilation device, comprising:
a hand-held housing having a light output window opening;
a light-generator mounted in the housing configured to generate high-intensity light in a broad ultraviolet to infrared spectral range suitable for effecting photo-epilation;
a control device configured to switch on the light-generator in brief pulses having a pulse duration of one of 1 ms to 2 ms, 1.1 ms to 1.9 ms, and about 1.8 ms such that the fluence on skin level is in the range from 2 to 7 J/cm$^2$ per pulse; and
a temperature sensor configured to sense a temperature of the light-generator, the temperature sensor is mounted in the housing and connected to the control device,
wherein light-generator is switched on only as long as the temperature is below a threshold temperature.

2. The photo-epilation device according to claim 1, further comprising a pulse trigger, wherein the control device is responsive to the pulse trigger to control the light-generating means to generate one pulse.

3. The photo-epilation device according to claim 1, wherein the control device is adapted to control the light-generating means at a pulse repetition frequency in the range from 0.1 Hz to 0.5 Hz.

4. The photo-epilation device according to claim 1, further comprising an input member coupled to the control device for selecting a skin type, wherein the control device is adapted to control the fluence settings in dependence upon the selected skin type.

5. The photo-epilation device according to claim 1, further comprising a skin-type detector mounted close to the window opening for receiving reflected light reflected backwards from the skin to generate a signal indicating a skin-type;
wherein the control device is coupled to the skin-type detector for receiving the signal, the control device is adapted to control the fluence settings in dependence upon the detected skin type.

6. The photo-epilation device according to claim 4, wherein the control device is adapted to set the fluence on skin level in the range selected from one of: 5 to 7 J/cm$^2$ for skin types I, II, III; 4 to 6 J/cm$^2$ for skin type IV; 3 to 5 J/cm$^2$ for skin type V; and 2 to 3 J/cm$^2$ for skin type VI; said skin types being indicated according to the Fitzpatrick skin-classification system.

7. The photo-epilation device according to claim 6, further having a user input configured to input a fine-setting within a scale ranging from MINIMUM to MAXIMUM, wherein the control device, in conformity with the user input between MINIMUM and MAXIMUM, is adapted to set the fluence on skin level in the range from: 5 to 7 J/cm$^2$ for skin types I, II, III; 4 to 6 J/cm$^2$ for skin type IV; 3 to 5 J/cm$^2$ for skin type V; and 2 to 3 J/cm$^2$ for skin type VI, said skin types being indicated according to the Fitzpatrick skin-classification system.

8. The photo-epilation device according to claim 1, further having a user input configured to input a setting within a scale ranging from MINIMUM to MAXIMUM, wherein the control device, in conformity with the user input between MINIMUM and MAXIMUM, is adapted to set the fluence on skin level in the range from 2 to 7 J/cm$^2$.

9. The photo-epilation device according to claim 1, wherein the device is configured to output light in the range from a low wavelength limit of approximately 575 nm to a high wavelength limit of at least approximately 1700 nm.

10. The photo-epilation device according to claim 1, wherein the light-generator comprises at least one Xenon flash lamp and a filter arranged between the light-generator and the window opening, the filter being selected to stop at least ultraviolet light and preferably selected to stop light below approximately 575 nm.

11. The photo-epilation device according to claim 1, further comprising at least one reflector arranged adjacent the lamp, opposite the window opening.

12. The photo-epilation device according to claim 1, further comprising a system of mirrors, mounted adjacent the window opening, for defining a light path for the light traveling from the light-generator to the window opening.

13. The photo-epilation device according to claim 1, wherein the light output window opening has a cross-sectional area of about 300 mm$^2$.

14. A photo-epilation device, comprising:
a hand-held housing having a light output window opening and a cross-sectional area of about 300 mm$^2$;
at least one Xenon flash lamp in the housing configured to generate high-intensity light in a broad ultraviolet to infrared spectral range suitable for effecting photo-epilation;
a filter arranged between the flash lamp and the window opening, the filter being selected to stop at least ultraviolet light;
a control device configured to switch on the flash lamp in brief pulses having a pulse duration of one of 1 ms to 2 ms, 1.1 ms to 1.9 ms, more preferably and about 1.8 ms; such that the fluence on skin level is in the range from 2 to 7 J/cm$^2$ per pulse, and a pulse repetition frequency is in the range from 0.1 Hz to 0.5 Hz; and
a temperature sensor to sense a temperature of the light-generator, the temperature sensor is mounted in the housing and connected to the control device,
wherein light-generator is switched on only as long as the temperature is below a threshold temperature.

* * * * *